US007183048B2

(12) United States Patent
Felkner et al.

(10) Patent No.: US 7,183,048 B2
(45) Date of Patent: Feb. 27, 2007

(54) KITS AND METHODS FOR DETERMINING THE EFFECTIVENESS OF STERILIZATION OF DISINFECTION PROCESSES

(75) Inventors: Ira C. Felkner, West Palm Beach, FL (US); Joseph P. Laico, New City, NY (US)

(73) Assignee: ICF Technologies, Inc., New City, NY (US)

( * ) Notice: Subject to any disclaimer, the term of this patent is extended or adjusted under 35 U.S.C. 154(b) by 0 days.

(21) Appl. No.: 10/244,895

(22) Filed: Sep. 16, 2002

(65) Prior Publication Data

US 2003/0064427 A1 Apr. 3, 2003

Related U.S. Application Data

(60) Provisional application No. 60/334,458, filed on Nov. 28, 2001, provisional application No. 60/322,248, filed on Sep. 15, 2001.

(51) Int. Cl.
*C12Q 1/00* (2006.01)
*C12Q 1/02* (2006.01)
*C12Q 1/22* (2006.01)

(52) U.S. Cl. .............................. 435/4; 435/29; 435/31

(58) Field of Classification Search .................... 435/4, 435/29, 31
See application file for complete search history.

(56) References Cited

U.S. PATENT DOCUMENTS

| | | | |
|---|---|---|---|
| 3,711,378 A | 1/1973 | Kereluk | |
| 3,968,250 A | 7/1976 | Boucher | |
| 5,186,946 A | 2/1993 | Valliéres | |
| 5,795,730 A | 8/1998 | Tautvydas | |
| 5,876,960 A | 3/1999 | Rosen | |
| 6,207,215 B1 | 3/2001 | Wilson et al. | |
| 6,287,518 B1 | 9/2001 | Ignacio et al. | |
| 6,498,041 B1 | 12/2002 | Tabacco et al. | |
| 6,599,715 B1 | 7/2003 | Vanderberg et al. | |

FOREIGN PATENT DOCUMENTS

| | | |
|---|---|---|
| EP | 0 433 053 A1 | 6/1991 |
| WO | WO 00/66763 A1 | 11/2000 |

OTHER PUBLICATIONS

Belliveau, et al., "Heat Killing of Bacterial Spores Analyzed by Differential Scanning Calorimetry", *J. of Bacteriol.*, vol. 174, No. 13, pp. 4463-4474 (Jul. 1992).
Beverly, et al., "A rapid approach for the detection of dipicolinic acid in bacterial spores using pyrolysis/mass spectrometry", *Rapid Commun. Mass Spectrom*, 10(4):455-8 (1996) (Abstract Only).
Brown, et al., "Release of dipicolinic acid and calcium and activation of *Bacillus stearothermophilus* spores as a function of time, temperature and pH", *J. Pharm. Pharmac.*, vol. 25, pp. 478-483 (1973).

Fitzpatrick, et al., "Sterilization of Bacteria by Means of Microwave Heating", *Journal of Clinical Engineering*, vol. 3, No. 1, pp. 44-47 (1978).
Goodacre, et al., "Detection of the dipicolinic acid biomarker in *Bacillus* spores using Curie-point pyrolysis mass spectrometry and Fourier transform infrared spectroscopy", *Anal. Chem.*, 72(1): 119-27 (2000) (Abstract Only).
Hindle, et al., "Dipicolinic acid (DPA) assay revisited and appraised for spore detection", *Analyst*, 124(11):1599-1604 (1999).
Loshon, et al., "Analysis of the killing of spores of *Bacillus subtilis* by a new disinfectant, Sterilox®", *Journal of Applied Microbiology*, 91:1051-1058 (2001).
Mallidis, et al., "The release of dipicolinic acid during heating and its relation to the heat destruction of *Bacillus stearothermophilus* spores", *Journal of Applied Bacteriology*, 59:479-486 (1985).
Paidhungat, et al., "Genetic requirements for induction of germination of spores of *Bacillus subtilis* by Ca(2+)-dipicolinate", *J. Bacteriol.*, 183(16):4886-93 (2001) (Abstract Only).
Phillipp, et al., "Repair and calcium dipicolinate release of bioindicators in propylene glycol and propylene glycol-water mixtures", *Journal of Applied Bacteriology*, 72:154-159 (1992).
Scott, et al., "Study of calcium dipicolinate release during bacterial spore gemination by using a new, sensitive assay for dipicolinate", *J. Bacteriol.*, 135(1):133-7 (1978) (Abstract Only).
Setlow, et al., "Mechanisms of killing spores of *Bacillus subtilis* by acid, alkali and ethanol", *Journal of Applied Microbiology*, 92:362-375 (2002).
Tabor, et al., "Rapid determination of dipicolinic acid in the spores of *Clostridium* species by gas-liquid chromatography", *Appl. Environ. Microbiol.*, 31(1): 25-8 (1976) (Abstract Only).
Tennen, et al., "Mechanisms of killing spores of *Bacillus subtilis* by iodine, glutaraldehyde and nitrous acid", *Journal of Applied Microbiology*, 89:330-338 (2000).
Warth, et al., "Determination of dipicolinic acid in bacterial spores by derivative spectroscopy", *Analytical Biochemistry*, 130:502-505 (1983).
Product Brochure, "Endospore Detection System", Ocean Optics, Inc., Website www.oceanoptics.com.
Rosen, D.L. "*Bacterial Endospore Detection Using Photoluminescence from Terbium Dipicolinate*" Reviews in Analytical Chemistry, Freund Publishing House, Tel Aviv, IL vol. 18 No. ½ XP000985266, ISSN: 0048-752X (Apr. 1999) pp. 1-21.

*Primary Examiner*—Ruth A Davis
(74) *Attorney, Agent, or Firm*—Flaster/Greenberg PC

(57) ABSTRACT

The invention relates to methods and kits and methods for assessing the effectiveness of a sterilization process by determining the release of dipicolinic acid (DPA) from bacterial or other spores that contain DPA. A biological indicator containing a spore may be included together with articles being sterilized, and an assay of DPA released from the spore can be performed moments after the sterilization process is completed, or during the process. The kits and methods thus provide a rapid and reliable method of assessing the effectiveness of a sterilization process and, consequently, assure the sterility of article subjected to the same process.

33 Claims, 9 Drawing Sheets

KITS AND METHODS FOR DETERMINING THE EFFECTIVENESS OF STERILIZATION OF DISINFECTION PROCESSES

CROSS-REFERENCE TO RELATED APPLICATIONS

This application claims the benefit under 35 U.S.C. § 119 of U.S. Provisional Application No. 60/322,248, filed Sep. 15, 2001, and U.S. Provisional Application No. 60/334,458, filed Nov. 28, 2001, the contents of each of which are incorporated herein by reference.

BACKGROUND OF THE INVENTION

Sterilization and disinfection processes, and the verification of the efficacy of such processes, are vital to the protection of the health and welfare of the general population. For example, sterilization and disinfection processes are of paramount importance in healthcare applications, food service applications, and even in some military and civil defense applications involving weapons of biological warfare. Sterilization processes are commonly applied to medical devices and equipment, instruments, food, water, containers for food and/or medical devices, laboratory spaces, hospital facilities, military and governmental facilities, and other physical spaces or articles where unwanted and potentially infectious pathogens may come in contact with human beings or other animals, causing infection. Because of the importance of such procedures, it is necessary to monitor the efficacy of each sterilization or disinfection procedure, to ensure that undesirable pathogens have been eliminated.

Sterilization is commonly understood to mean that, upon completion of the sterilization process, the treated article or space is characterized by a complete absence of viable microorganisms. "Disinfection," in contrast, is indicative of processes used to reduce the level of pathogens in an area or on an article to a degree such that they would pose minimal risk of infection to a healthy person. Disinfection methods include application of hydrogen peroxide, ethanol, or chlorine bleach. Commonly used methods of sterilization include "hot" or heat-based methods, such as sterilization by dry heat or sterilization by moist heat (steam) and "cold" or low temperature methods, such as sterilization by ethylene oxide, peracetic acid, formaldehyde, gas plasma sterilization, e.g., using a hydrogen peroxide plasma, and radiation, such as gamma radiation or E-beam radiation.

Conventional practice, particularly in the area of medical and scientific devices, has been to accomplish the sterilization process by use of moist heat (most commonly using autoclave equipment). In more recent practice, particularly in the healthcare industry where implements and devices are becoming more and more delicate and made of diverse materials, such as plastics, low temperature sterilization processes are favored. For example, sterilization using gas plasmas and/or ethylene oxide is routinely used. Specialized sterilization equipment has been developed for use of these sterilization procedures. For example, the STERRAD® System (Advanced Sterilization Products, a Johnson & Johnson Company (Irvine, Calif.)) uses hydrogen peroxide vapor low temperature gas plasmas to sterilize medical devices.

It is necessary to monitor or evaluate the efficacy of processes used to sterilize or disinfect in order to assure that the sterilized equipment is safe for use. Commonly used means of monitoring the sterilization process(es) is by use of a sterilization process indicator. The sterilization process indicator is placed in close proximity to the products, articles, and/or in the space which is to be sterilized, and is subjected to the same sterilization procedure.

In general, there are two types of sterilization process indicators: (i) physical/chemical sterilization process indicators; and (ii) biological sterilization process indicators. A physical/chemical process indicator is used to measure directly or indirectly the adequacy of the physical sterilization conditions during the sterilization process (such as temperature, pressure, and/or contact with a specific chemical). For example, a physical/chemical sterilization process indicator may be formulated to change from a dark green to a bright green when the indicator has been subjected to a specific high temperature for a specified amount of time. By observing the change from dark green to light green, the person carrying out the sterilization procedure is assured that at least the temperature process parameter of the procedure is met, and may extrapolate that all pathogens present on the articles subjected to the process have been destroyed. However, physical/chemical sterilization process indicators verify the presence or absence of certain physical or chemical conditions, and therefore only indirectly reflect upon the viability or non-viability of pathogenic organisms present. They are not a direct measure of the survival or destruction of any bacteria or pathogens initially present on the articles or in the space.

In contrast, biological sterilization process indicators permit a more direct assessment of the viability or non-viability of a living organism subjected to the sterilization procedure. Biological sterilization process indicators or biological indicators (BIs) generally consist of a known number of microorganisms of known resistance to the selected mode of sterilization ("the indicator organism"), in or on a carrier, and enclosed in a protective package. The biological sterilization process indicator, like the physical/chemical process indicator, is subjected to the same sterilization processes of the article and/or space to be sterilized and, upon completion of the sterilization procedure, the viability/non-viability of the organisms is assessed through various means.

When using a BI, the degree of sterilization or disinfection may conventionally be expressed in terms of "log kill"—the number of orders of magnitude by which the known population of indicator organism is decreased by the sterilization/disinfection process. Under present FDA regulations (21 C.F.R. § 800 et seq.), a six log reduction ("6 log kill" or Sterility Assurance Level (SAL) of $10^{-6}$) is considered to be sufficient assurance that "sterilization" has been accomplished for medical devices intended to come in contact with breached skin or compromised tissue. A different log reduction may apply, depending on the intended use of the device or object to which the process has been applied.

Because the resistance or susceptibility of the indicator organism will necessarily influence the sterility assurance analysis, the indicator organism is selected to be more resistant to the chosen sterilization technique than the microbial, fungal, or viral population anticipated to be present on the non-sterile devices or in the non-sterile space. The resistance to sterilization is conventionally indicated by the D value or the Z value of a given organism under specific sterilization conditions. The D values and Z values of a given organism are determined in accordance with the published guidelines of the United States Pharmacopecia (USP).

Because of their known D values, commonly used indicator organisms include *Bacillus stearothermophilus* (for steam/moist heat sterilization procedures), *Bacillus subtilis* var. *niger* (ethylene oxide, hydrogen peroxide, or dry heat), *Bacillus pumilus* (radiation). Also commonly used are bacteria of the genus *Clostridium* (*Clostridium sporogenes*), *Candida albicans*, *Aspergillus niger*, *Micrococcus luteus*, *Pseudomonas aeruginosa*, *Staphylococcus aureus*, and *Escherichia coli*, as well as those organisms classified in Group 18, in Bergy, et al., *Bergy's Manual of Determinative Bacteriology*, 9$^{th}$ ed., Lippincott, William & Wilkins, 1999, the contents of which are incorporated herein by reference. In conventional practice, the indicator organism may be vegetative cells or endospores (spores).

A standard type of biological sterilization process indicator is a device containing or including a known population of bacterial spores. The indicator is placed into a sterilization chamber (or at the site of sterilization or disinfection) and subjected to a sterilization process, along with the objects or articles to be sterilized or disinfected. Subsequent to the completion of the sterilization procedure, the indicator spores are contacted with a sterile growth medium and incubated for a selected period under conditions which favor germination of the spores and proliferation of vegetative cells. Growth of bacterial cells, determined by, for example, the presence or absence of certain metabolic products, or by observation of plated culture suspensions, indicate that the sterilization process was insufficient to destroy all of the spores, and therefore, that the process may not have achieved suitable sterilization or disinfection of the articles that accompany the indicator through the process. Although a wide variety of devices for containing the spores of the biological indicator has been developed, there are few variations in the general process of assessing the viability of the indicator organism following completion of the sterilization process. All involve an observation of the presence or absence of bacterial growth, post sterilization process.

Many biological indicators are self contained, in that they comprise spores and/or vegetative bacterial cells and germination/culture medium in a single container, typically in separate compartments. Following sterilization, the spores are combined with the medium, and the entire container is incubated in order to allow for the detectable growth to occur. Other known biological indicators comprise spores disposed in or on a carrier. After being exposed to the sterilization process, the carrier is contacted with a germination/culture medium to allow detectable growth from the spores to occur.

Like the physical/chemical sterilization process indicators, conventional BIs have several drawbacks. First, use of the conventional biological sterilization assurance process does not allow one to rapidly determine whether the sterilization process to which the indicator has been subjected was sufficient to destroy an adequate number of the spores in the indicator, and therefore does not permit rapid evaluation of the efficacy of the sterilization procedure. Because the spores of biological indicators require that the viability assessments be accomplished by permitting sufficient time such that the growth or lack of growth of the indicator organism can be assessed, rapid turn around time of, for example, medical devices, is impossible. In most cases, the incubation time required for a viability assessment is approximately forty-eight hours. During the time that the viability of the indicator organisms is being assessed for growth, the sterilized articles cannot be used safely.

In smaller facilities, such as outpatient clinics, which often lack microbiology labs, the organisms of the BIs must be sent to other facilities for cultivation and viability assessment after application of the process, further adding to the delay and costs in obtaining results. Many healthcare facilities have limited resources; they must reuse their sterilized instruments as soon as possible, preferably immediately or soon after sterilization or disinfection. Thus, the delay between sterilization and confirmation of sterility or sterility assurance is often expensive and impractical. Further, during and after the indicator organism is being cultured, accurate results rely on the maintenance of a sterile atmosphere and consistent practice of aseptic technique on the part of laboratory technicians. Hence, the assessment process is susceptible to human error. A need in the art exists for a more rapid method of assessing the efficacy of a sterilization procedure.

Prior art attempts have been made to overcome the time delay inherent in the use of biological sterilization process indicators. For example, a system has been developed that correlates sterilization efficacy with the activation (or deactivation) of one or more thermostable enzymes present in the indicator organism. However, such systems provide again, only an indirect confirmation of sterility, and further, are not useful in connection with other non-heat based or "cold" sterilization methods, which would not serve to reliably deactivate thermostable enzymes. Additionally, because the outcome of sterility assurance tests based on evaluation of the inactivation of thermostable enzymes requires detection of a negative result (the absence of enzyme activity), it is fraught with potential errors. For example, inactivation of enzyme activity can have multiple causes, such as errors in assay performance (human error, technical failures), deficiency in enzyme substrate, or inactivation of the enzyme attributable to a cause other than the sterilization procedure.

Most commonly, the indicator organism selected for use in a biological process sterilization indicator is a bacterial endospore. Spores are preferred because they exhibit, overall through all species, a greater resistance to various sterilization methods, including heat sterilization, chemical sterilization (wet or plasmas), and radiation sterilization, and therefore always have greater D and/or Z values than their vegetative cell counterparts.

Dipicolinic acid ("DPA"; pyridine-2,6-dicarboxylic acid) is a component of bacterial spores, including spores of the genus *Bacillus*. Dipicolinic acid is represented by the structure:

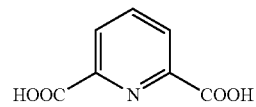

In nature, DPA is present in spores as a substantially insoluble calcium salt (calcium dipicolinate), and is released upon the germination of the spore. While not wishing to be bound by theory, it is believed that DPA is present in the cortex and coat of the bacterial spore in an amount of about 10% to about 15% of total spore weight, and is present primarily in the form of calcium dipicolinate.

As it is not present in vegetative, non-sporulating bacterial cells, DPA has been suggested in the art as an indicator for the presence and quantification of bacterial spores (Hindle, et al., 1999, Analyst 124:1599–1604; U.S. Pat. No. 5,876,960). It has been recognized that the release of DPA from spores occurs after heat-induced loss of viability of the spores (Mallidis, et al., 1985, J. Appl. Bacteriol. 59:479–486) and upon germination of the spores (Scott, et al., 1978, J. Bacteriol. 135:133–137). However, other processes or conditions which induce the release of DPA from the spores have not been elucidated in the art, and no correlation between the release of DPA and the destruction of the spore has previously been disclosed.

BRIEF SUMMARY OF THE INVENTION

The invention described herein provides a method for assessing the effectiveness of a sterilization process and/or for assuring the sterility of an article to which a sterilization process has been applied. The method includes subjecting a biological indicator that includes a spore that contains dipicolinic acid to a sterilization process and determining a release of dipicolinic acid from the spore. The release of dipicolinic acid from the spore indicates the effectiveness of the sterilization process. The method may include an additional step of assessing the viability of the spore, after the sterilization process.

The determination of a release of dipicolinic acid from the spore may be accomplished by chromatographic analysis or by spectroscopic analysis, such as derivative ultraviolet spectroscopic analysis, where the determination is accomplished in the presence or the absence of an ionized lanthanide.

Also provided by the invention are kits for determining the effectiveness of a sterilization process. The kits include a biological indicator that includes a spore that contains dipicolinic acid and a control sample.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
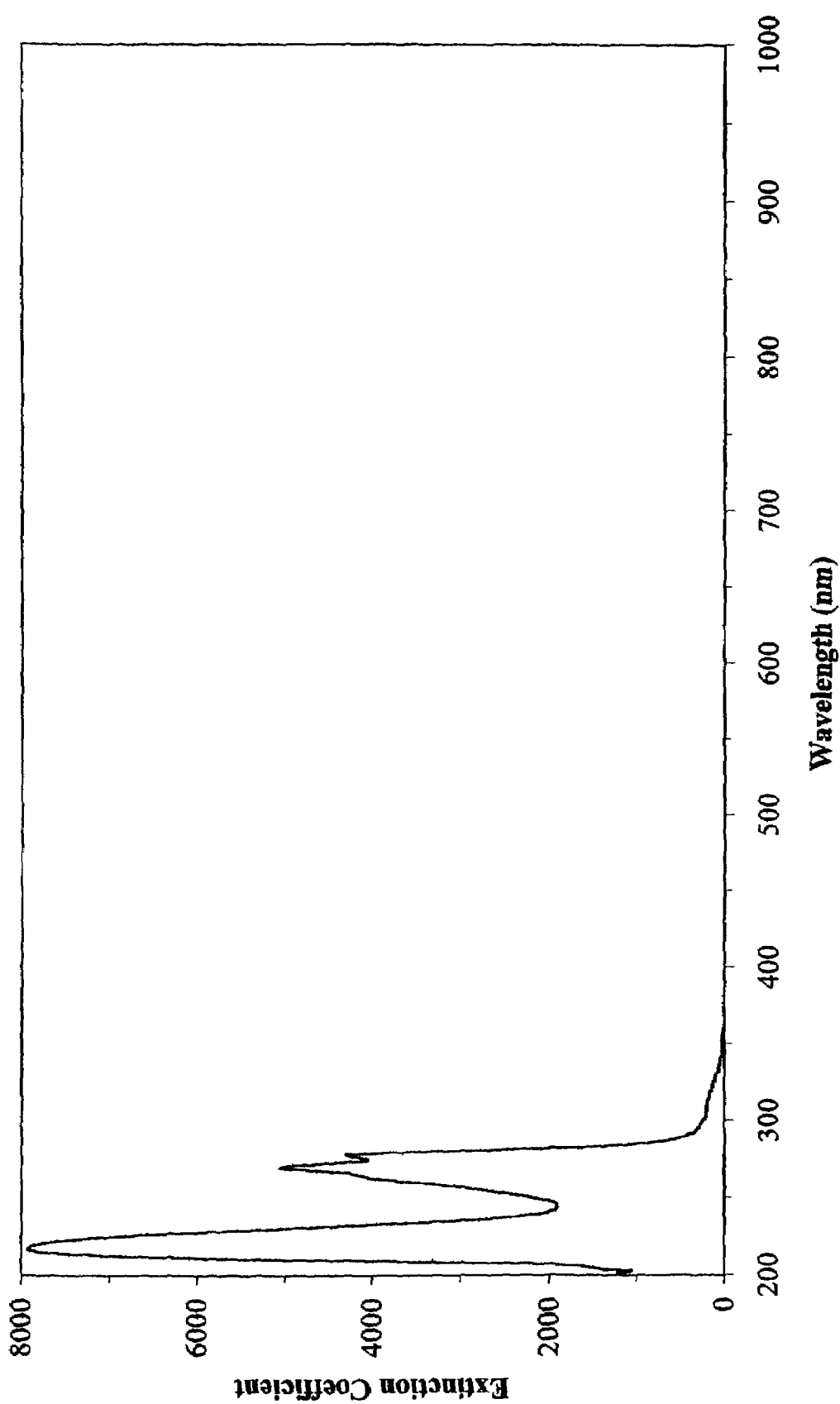
FIG. 1 shows the extinction spectra of dipicolinic acid. Absorbance or optical density at a given intensity can be calculated using the Beer-Lambert equation where absorbance $(A)=\epsilon cl$, where $\epsilon$ is the extinction coefficient, c is the concentration of the compound, and l is the length of the path length.

The invention is based on the discovery that endospores release dipicolinic acid (DPA) upon application of sterilization methods of all or substantially all types that destroy or otherwise compromise the spore coat and/or spore cortex. Without wishing to be bound by theory, it is believed that spore death or inactivation occurs slightly prior to release of dipicolinic acid from the spore coat. Thus, as described herein, it has been discovered that spore non-viability or inactivation can be correlated with DPA release from spores to which sterilization processes have been applied. Therefore, the release of DPA from spores in the biological indicator can be correlated with the sterilization of articles simultaneously subjected to the same sterilization process.

The invention includes a method for determining the effectiveness of any of a variety of sterilization processes, for example, sterilization treatments or disinfection treatments, methods for assuring the sterility of articles subject to a sterilization process, and kits for use in carrying out the methods. The methods described can be performed almost immediately upon completion of the sterilization process and provide a sensitive and accurate indication of the effectiveness of the sterilization process and/or the sterility of articles to which the process was applied. The methods can be performed upon completion of the sterilization process, or simultaneously (continuously) with the sterilization process, provided that the sterilization process does not interfere with the selected procedure for determining the release of DPA from the spore of the biological indicator. The methods thereby obviate the need for complex and time consuming culture-based methods for assessing spore viability by germination. Using the methods described herein, one can sterilize or disinfect articles and, rapidly, within minutes or hours of completion of the process, confirm the sterility of such objects.

As used herein, the term "viable" with reference to a spore, describes a spore that is capable of germinating and vegetatively proliferating when maintained at culture conditions that are characteristic of the organism from which the spore was obtained. Alternatively, the viable spore is capable of germinating and forming a vegetative cell upon application of external conditions which are known in the art to cause germination and proliferation of the spore, such as, for example, heat shock. Culture conditions generally include incubation within a selected temperature range in a nutrient-containing environment, and are well-known in the art. Conditions suitable for the induction of "heat shock" are also well-known to the skilled artisan, and include, for example, subjecting the spores of any of the several Bacillus species, e.g., B. subtilis, at about 70° C. for about ten minutes and maintaining the spores of any of the several Clostridium species, e.g., Clostridium beijerinckii, at about 100° C. for about five minutes.

By "cold sterilization process" or "low temperature sterilization process", it is meant a sterilization process that does not require heating of the article to a temperature significantly greater than approximately ambient temperature, for example, no greater than about 60 to 75° C. Examples of cold sterilization process include application of sterilization agents, such as microwaves, ultraviolet light, ethylene oxide, gas plasmas, e.g., $H_2O_2$ plasma, ethanol, formaldehyde, oxidizing compounds, e.g., those having oxidation reduction potentials of 500 mV or greater, peracetic acid, iodine (e.g., BETADINE®, Purdue Pharma, L.P., Ardsley, N.Y., U.S.A.), nitrous acid, strong acids, strong alkalis, super-oxidized water, hypochlorous acid, or other microbial agents known or developed in the art such as, for example, the commercially available agents sold under the trademark STERILOX® (Sterilox Technologies, Yardley, Pa., U.S.A.; a super-oxidized water compound containing hypochlorous acid) and STERRAD® (Johnson & Johnson, Co., Irvine, Calif., U.S.A.; hydrogen peroxide low temperature gas plasma). It is understood that cold sterilization methods can be performed sequentially or simultaneously with heat-based sterilization methods (for example, combined application of heat and ultraviolet light).

By "heat based sterilization" or "hot sterilization" methods, it is meant those sterilization processes that involve subjecting the articles to be sterilized to high temperatures and/or high pressures (e.g., 121° C.). Autoclaves are most commonly used to apply hot sterilization methods, although methods using baking are also known.

"Dipicolinic acid" (DPA) as used herein, refers to relatively water-soluble forms of dipicolinate (pyridine-2,6-dicarboxylic acid), including, for example, the free base form, the protonated acid form, and various salt and chelate forms of dipicolinate.

A "biological indicator" is a device which contains, supports, or carries at least one spore ("indicator organism"), and which can be recovered upon completion of a sterilization process. The physical configuration of the biological indicator will necessarily vary, depending on the type of spore(s) selected, and the particular sterilization process to be used. Examples of biological indicators which can be used in the methods of the present invention include containers, vials, ampoules, capsules, cups, jugs, dishes, membranes, envelopes, sticks, films or sheets, filtration media, and absorbent materials such as paper, cardboard, cotton, fibers, or sponge (natural or synthetic). The materials of which the biological indicator is made may be autoclavable.

A biological indicator is "autoclavable" if it can be subjected to 15 p.s.i.g. steam for at least fifteen minutes without substantially inhibiting the recoverability of spores from the biological indicator. For example, a plastic support having spores adsorbed to its surface is not autoclavable if it melts when subjected to 15 p.s.i.g. steam for fifteen minutes and the spores cannot be rinsed from its surface by immersing the surface in water.

"Derivative spectroscopy" as used herein, refers to a spectrographic method in which the absorbance of a sample is measured over a range of wavelengths, and from which the measurements are expressed in terms of the rate of change of the absorbance of the sample with the rate of change of the wavelength (d[absorbance]/d[wavelength]).

"Multi-angle light scattering analysis" of spore viability, as used herein, refers to the process described in PCT patent application having the International Publication No. WO 00/66763, which is incorporated herein by reference, or any equivalent procedure.

As used herein "sterility" or "sterile" refers to the non-occurrence of bacteria, bacterial spores, molds, viruses, and other microorganisms in any form in which they are capable of germinating, growing, proliferating, or infecting a second organism. It is understood that complete absence of microorganisms is not usually required in order for an article or a space to be considered safe for use in its intended purpose by or in humans or other animals. Depending on the intended use, varying degrees of sterility and/or disinfection may be determined by the methods of the invention. For example, in some medical device applications, a six log reduction ("a 6 log kill" or a 1,000,000-fold decrease) in the number of viable microorganisms in the BI is generally considered to be indicative that a sufficient level of sterility has been achieved. Thus, for example, if a sterilization process serves to decrease the number of viable spores in the biological indicator as described herein by a $10^6$-fold or greater, as assessed by detection of the release of DPA, then the article subjected to the same treatment will generally be considered "sterile" for several purposes. However, it is understood that particular uses can require larger or smaller fold changes in the number of spores that survive in the biological indicator, and such variations are encompassed within the terms "sterile" and "sterility" as used herein. Similarly, a "sterilization process" as used herein is a process that reduces the population of viable microorganisms to the desired level, and therefore, as used herein, encompasses the continuum of non-occurrence of microorganisms from "sterilization," as described in FDA regulations to "disinfection." Accordingly, a "sterilization process," as used herein is considered to be effective, if the desired reduction of microorganisms upon completion of the sterilization process has been achieved.

An apparatus is "adapted to fit" an analytical instrument if the apparatus has a size, form, shape, composition, and/or configuration that facilitates performance by the instrument of the analysis for which the instrument is intended. For example, many commercially available spectrophotometers have a sample compartment which is aligned with the incident light beam and which accommodates a cuvette having a width of 1 centimeter, a depth of 1 centimeter, and a height of at least one to two centimeters. Various apparatus can be adapted to fit such instruments, if they have a portion having a 1 centimeter square cross-section, and a length of a few centimeters, and have optically clear windows in the path of incident light.

The invention includes a method of assessing the effectiveness of the sterilization process, as well as a method for use in the assurance of sterility of an article subjected to a sterilization process. After or during the carrying out of the sterilization process, spores contained within or on the biological indicator are removed and, a determination is made as to whether dipicolinic acid has been released. Such determination may be made using, for example, a spectrophotometer, and in the presence of an ionized lanthanide. A determination that dipicolinic acid has been released indicates that at least some of the spores of the biological indicator have been deactivated. The release or rate of release of dipicolinic acid from the spores can be correlated with inactivation or non-viability of any pathogens which may be present on articles that were or may be subject to the same sterilization process.

In producing the methods of the invention, one or more biological indicators, depending on the scale of the sterilization process to be run, is subjected to a sterilization process. The sterilization process for use in the practice of the inventive method may be any sterilization process known or to be developed in the art that accomplishes sterilization or disinfection by disrupting, compromising, or otherwise disturbing the spore coat and/or cortex of the indicator organism, such that the release of dipicolinic acid is effected.

The selected sterilization process may be either a hot sterilization process or a cold sterilization process. Suitable processes for use in the practice of the invention include, but are not limited to, heat sterilization (dry or moist), such as the moist heat sterilizations carried out using an autoclave; sterilization by gas plasmas, sterilization by application of hydrogen peroxide, peracetic acid, formaldehyde, iodine or iodine-based compounds (e.g., BETADINE®, glutaraldehyde, nitrous acid, super-oxidized water, hypochlorous acid, strong acids, strong alkali, ethanol, and other oxidizing agents having an oxidation potential of greater than 500 mV. Preferred are sterilization processes using the commercially available compound STERELOX® Sterilox Corporation, Yardley, Pa., U.S.A.) and/or STERRAD® (Advanced Sterilization Products, Johnson & Johnson Company, Irvine, Calif., U.S.A.).

The selected sterilization process may be carried out on any apparatus known or to be developed that is suitable for practice of the particular sterilization process. For example, the sterilization process using gas plasma and hydrogen peroxide can be carried out using the STERRAD® equipment available from Advanced Sterilization Products, Johnson & Johnson Company. Similarly, moist heat sterilization processes may be applied using an autoclave.

The methods and kits described herein include a biological indicator. The biological indicator includes spores that contain dipicolinic acid. The type or species of organism from which the spores are obtained is not critical, so long as the selected spores contain dipicolinic acid in its cortex or coat. Dipicolinic acid is known to occur in the spores of most bacterial species, and has been reported in some mold species, e.g., *Penicillium citreo viridae*.

Types of spores which may be included in the biological indicator of the invention include, but are not limited to, spore(s) of a bacterium of the genus *Bacillus*, spore(s) of a bacterium of the genus *Clostridium* spores, *Bacillus subtilus*, spores of *Bacillus stearothermophilus*, and spores of *Candida albicans*. Other organisms from which spores may be obtained include *Bacillus anthracis, Clostridium botulinum, Clostridium beijerinckii*, spore(s) from a bacterium of the genus *Sporosarcia*, such as *Sporosarcine ureae*, and spores of other gram positive bacteria including, for example, those classified as Group 18, in Bergy, et al., 9th ed., *Bergy's Manual of Determinative Bacteriology*, Lippincott, William & Wilkins, 1994, the contents of which are incorporated herein by reference. The spores can be in any form: powdered, freeze-dried, or air-dried; they may be impregnated into a sponge or fibrous mass or they may be in a liquid suspension. If a conventional viability analysis is to be carried out in addition to the detection of dipicolinic acid, the spores of the BI may be suspended in a growth medium.

It is preferred that the spore or spores selected for use in a biological indicator is a spore(s) known to exhibit resistance to the selected sterilization process. For this reason, spores of *Bacillus subtilis* (particularly *Bacillus subtilis globigii*), *Bacillus stearothermophilus*, and *Clostridium sporogenes* are preferred, especially when "hot" sterilization processes are to be employed.

The number or population of spores that are to be included in or on the biological indicator may be variable, and need not be known precisely. It should be sufficiently high that the release of DPA from the spores can be detected using the selected DPA detection method. For example, if the selected detection method is highly sensitive, the BI may comprise one spore. It is preferred but not required that the biological indicator comprises about 106 spores or greater.

The biological indicator to which the spore or spores is attached, contained, or otherwise associated with can take any configuration, so long as such configuration permits the handling of the spore(s) and the determination of the release of DPA from the spore(s). Further, the biological indicator should have physical configuration that allows for exposure of the spore(s) to the sterilizing agent; accordingly, the configuration will necessarily vary, physically and/or in the material used for the biological indicator, depending on the selected sterilization process. The biological indicator may be of a relatively simple construction, such as a glass vial having a screw cap, which, for example, may contain a powdered spore preparation. Examples of configurations for the biological indicator that are containers include vials, ampoules, sheets or films, membranes, capsules, packets, envelopes, sponges, textiles, fibers, cotton batting, plates, cups, sticks, beakers, bottles, etc. Using the example of a vial having a screw cap and containing a powdered or dry spore preparation, if a gaseous sterilizing agent is used, then the cap should be sufficiently loosened during the sterilization process that the agent can reach the spores within the vial, assuming the vial and the cap are otherwise impermeable to the agent.

Similarly, if the biological indicator includes a container containing spores and the container is manufactured of a material that is impermeable to the sterilizing agent used in the sterilization process, then the container should be opened or rendered permeable to the agent before treating the biological indicator according to the sterilizing process.

The biological indicator may be made from any material known or to be developed in the art, as long as the selected material is able to withstand the selected sterilization process without undergoing any physical and/or chemical degradation that would interfere with the detection of dipicolinic acid. For example, the biological indicator may be made from material that is resistant to chemical or physical attack by substantially all traditional sterilization methods (e.g., glasses, such as borosilicate glass). Alternatively, the biological indicator may be made from material that is merely resistant to the sterilization agents for which its use is intended. Suitable materials may include, without limitation, metals, ceramics, plastics, elastomers, rubbers, paper, cardboard, wood, cloth, etc.

For example, if a cold sterilization process is to be employed, a non-heat resistant or non-autoclavable biological indicator can be utilized. Alternatively, if the sterilization process is to be accomplished by use of an autoclave, the biological indicator should be autoclavable, but need not be resistant to chemical attack.

The biological indicator may also have in it or on it any compounds or materials as known or to be developed in the art which serve to facilitate the detection of DPA. For example, if the release of dipicolinic acid is to be detected using excitation/emission spectroscopy, the biological indicator may include a lanthanide salt, such as salts of cerium, praseodymium, neodymium, promethium, samarium, europium, gadolinium, terbium, dysprosium, holmium, erbium, thulium, ytterbium, and/or lutetium. Terbium salts are preferred if the detection method is to be spectroscopy using ultraviolet light for excitation and visible light for emission.

The BI of the invention is subjected to the sterilization process; a determination is then made as to whether dipicolinic acid was released from the spore(s) included in or on the biological indicator. One can make such determination by detecting the presence or absence of released calcium dipicolinate or by released free dipicolinic acid. Determinations may be accomplished by any method known or developed in the art for the detection of the presence or absence of dipicolinic acid in a sample. Suitable methods include, for example, those described in Warth, 1983, Anal. Biochem. 130:502–505: Hindle, et al., 1999, Analyst 124:1599–1604; U.S. Pat. No. 5,876,960; Porter, et al., 1967, Biochem. J. 102:19C; Scott, et al., 1978, J. Bacteriol. 135,133–137; Tabor, et al., 1976, Appl. Environ. Microbiol. 31:25–28; Watabe, et al., Nippon Saikingaku Zasshi 43:927–930; Louis, 1967, Anal. Biochem. 19:327–337; Goodacre, et al., 2000, Anal. Chem. 72:119–127; Beverly, et al., 1996, Rapid Commun. Mass Spectrom. 10:455–458, the contents of each of which are incorporated herein.

If methods for detection of dipicolinic acid using spectroscopy, particularly excitation/emission spectroscopy with a first derivative analysis, are selected, lanthanide photoluminescence can be used to enhance quantitation of dipicolinic acid during the detection process. A preferred lanthanide for enhancement of photoluminescence in a visible light range is terbium. Any type or model of spectrophotometer can be used, as in known or to be developed in the art, including those configured so that detection can be accomplished using a probe placed directly into the biological indicator of the invention.

Some procedures of dipicolinic detection are not capable of distinguishing between dipicolinic acid released from spores and dipicolinic acid associated with spores (which is generally in the form of the substantially water-insoluble calcium dipicolinate associated with sporular debris). If such procedures are employed in the methods of the invention, it may be desirable to separate spore debris from a sample suspension prior to determining the presence or absence of free dipicolinic acid and/or a lanthanide/dipicolinate complex in the suspension. A variety of techniques such as filtration, ultrafiltration, antibody-mediated agglutination, and centrifugation are known for removing debris from a suspension, and any of these techniques can be used in the practice of the methods of the invention, as is known or to be developed in the art.

Upon removal of spores from the suspension, the presence or absence of dipicolinic acid in a clarified solution can be assessed by using, for example, gas chromatography, thin layer chromatography, high pressure chromatography, or other chromatographic methods, as is known or to be developed in the art.

If the use of spectroscopic analysis is employed as disclosed herein, it is not necessary to remove spores or spore debris from a suspension in order to determine whether or not dipicolinic acid has been released by the sterilization process.

Additionally, in one embodiment of the method of the invention, light is transmitted through a suspension from which spores and spore debris have not been removed, and is analyzed in both the ultraviolet and visible regions of the spectrum. In this embodiment, transmitted ultraviolet light can be analyzed to perform spectroscopic analysis of the suspension, and transmitted visible light (in the presence of a lanthanide) can be used to perform light emission analysis of the suspension. The ultraviolet and visible light analyses may be performed simultaneously or sequentially in any order.

A preferred procedure for determining whether or not dipicolinic acid has been released from the spore by the sterilization process is by derivative ultraviolet spectroscopic analysis (DUVS). DUVS is performed by measuring the absorbance values at a variety of wavelengths and describing those data in terms of the derivative absorbance with respect to wavelength (i.e., d{absorbance}/d{wavelength} at approximate wavelengths of 220, 235, 260, 268, 278, and/or 280 nanometers). Thus, DUVS can be used to analyze d{absorbance}/d{wavelength} at one or more of these wavelengths in order to quantify the amount of dipicolinic acid in a particular sample, and/or in a control sample. DUVS can also be used to qualitatively assess the rate of change of absorbance or d{absorbance}/d{wavelength} at any or all of these wavelengths, in order to assess the rate of change of the release of dipicolinic acid during the course of or after completion of the sterilization process.

If desired, the methods of the invention can be performed alone, or, in combination with other more conventional methods of assessing spore viability. Such more conventional methods include maintaining spores at culture conditions in which germination of the spores and proliferation and growth of organisms therefrom is facilitated. For example, plating procedures as well as direct microscopic counting techniques may be used. Also, spore viability can be determined using multi-angle light scattering analysis of a spore suspension, for example, as disclosed in International Patent Application having the Publication Number WO 00/66763, the contents of which are incorporated herein by reference, or by use of visible light spectrophotometric analysis. Such conventional methods of determining viability can be used to confirm or ensure that the results obtained by analysis of DP A accurately correlates to a desired sterility level. Other methods include those described in U.S. Pat. Nos. 3,770,351; 5,795,730; and 5,876,960, the contents of each of which are incorporated herein by reference.

When practicing the methods of the invention, one may subject the biological indicator to the sterilization process, then subsequently determine whether dipicolinic acid is released from the spore(s), or, one may conduct the sterilization process and the determination of the release of dipicolinic acid simultaneously. If the latter option is pursued, one may conduct the analysis of the release of DPA by obtaining samples substantially continuously during the sterilization process.

After the biological indicators are subjected to the sterilization process, or during the course of the sterilization process, the spores or aliquots of the spores contained within the biological indicator are removed, and the release of dipicolinic acid from the spores or fraction of spores is determined, for example, using the methods described above, including DUVS. Release of dipicolinic acid from the spores indicates that at least some of the spores have been inactivated, or have become non-viable. The rate of dipicolinic acid released from the spores over time during a sterilization process, or, the quantity of dipicolinic acid released from the spores upon completion of a sterilization process, can be correlated with the likelihood that the microorganisms which may be present on other articles simultaneously subjected to the same sterilization process have survived or have been inactivated. In this way, determination of whether dipicolinic acid has been released from the spores of the biological indicator can indicate the effectiveness of the sterilization process, as well as the sterility of any articles or objects included in the sterilization procedure with the biological indicator.

In practicing the methods of the invention, a person of ordinary skill can easily prepare or devise standards to which the rate of release of the DPA from the spores of the biological indicator or the total quantity of release of dipicolinic acid from the biological indicator can be evaluated against, in order to determine the effectiveness of the sterilization procedure, and therefore, the sterility of articles included in the sterilization process with the biological indicator. For example, release of dipicolinic acid can be calculated as a fractional release by comparing the amount of dipicolinic acid released from the spores of the biological indicator with the total known dipicolinic acid content of the spores of the biological indicator. If a specific spore population of $10^6$ spores is utilized in the biological indicator, and it has been determined, through empirical means known in the art, that such spores contain 10% by weight of dipicolinic acid, one can compare the empirically-determined quantity of dipicolinic acid released after or during the sterilization process with the calculated amount of dipicolinic acid known to be present in the specific spores, in order to determine whether the sterilization process has been successful.

Release of dipicolinic acid from the spores can be determined by detecting the amount of dipicolinic acid released from the spores, by detecting the amount of dipicolinic acid not released from the spores, or by both mechanisms. The amount of DPA not released may approximately correlate with the number of intact and therefore potentially viable spores. In the event that the determination of a very small amount of dipicolinic acid is desired, the sensitivity of the spectrophotometric methods described herein can be enhanced, as discussed above, by assessing the dipicolinic acid in the presence of ionized lanthanide metal atoms (e.g., terbium ions or ions of any of the other elements of atomic numbers 57–71, inclusive) in solution. Release of substantially all dipicolinic acid from the spores of the biological indicator is an indication that substantially all spores have been inactivated. However, because it is believed that spores can be inactivated upon release of less than all dipicolinic acid contained in the spores, relative assurance of sterility of articles subjected to the same sterilization process and/or the effectiveness of that sterilization process can be had, even in the absence of complete release of dipicolinic acid from spores of the biological indicator.

To obtain assurance that the pathogens of articles subjected to a sterilization process have been destroyed, in the absence of the release of the entire amount of dipicolinic acid present in the spores, a person of ordinary skill may set up a series of simple empirical standards for comparison. For example, aliquots of a single spore preparation can be subjected to different degrees or parameters of the selected sterilization process (e.g., for various lengths of time, at various concentrations of sterilizing agents, or at various intensities of sterilizing agents). The treated aliquots can then be incubated according to standard culture techniques in order to facilitate the germination of any spores which may have survived the treatment and the resulting proliferation of the vegetative cells. The quantity of dipicolinic acid released from each of the aliquots can be separately determined, using any of the techniques described herein. Release of the dipicolinic acids from each of the spore aliquots can thereby be correlated with the likelihood that the spores survived the treatment to which they were subjected.

Alternatively, or in addition to, the process described above, aliquots of a spore preparation can be treated together with aliquots of other microorganisms, and release of dipicolinic acid from the spores can be correlated with survival of the other microorganisms (i.e., assessed using culture methods suitable for the particular microorganisms).

Once such data have been generated, the release of dipicolinic acid from the spore(s) of the biological indicator of subsequent runs of the selected sterilization process can be correlated with the effectiveness of the sterilization process, and used as an indication of the sterility of any articles included in the sterilization process with the biological indicator.

As is easily recognized by one of skill, the establishment of standards showing the relationship between spore inactivation and the amount or rate of dipicolinic acid release need not be performed by the same individual or entity which wishes to assess the effectiveness of the sterilization process. Instead, the standards using a batch of spores can be prepared by a first party, and based upon that testing, a description of the relationship between the quantity or rate of dipicolinic acid released from the spores and the loss of viability of the spores can be provided to a second party, together with one or more aliquots with the same batch of spores contained within a biological indicator, or with instructions as to the preparation of a biological indicator. The second party, if necessary, may include the spores in a biological indicator, and can use such indicator to evaluate the effectiveness of a sterilization process by subjecting the indicator to the sterilization process, evaluating the release of dipicolinic acid from the spores, and comparing the quantity or rate of release to the standard provided by the first party.

Similarly, the first party may determine a relationship between the rate and/or quantity of dipicolinic acid released from a batch of spores, and a loss of viability of a different microorganism, for example a microorganism other than the one from which the spores were obtained, or a mixture of such organisms. The second party may use that standard data to assess loss of viability of the different microorganisms attributable to a sterilization process, by determining the rate or quantity of dipicolinic acid release from the same batch of spores in or on a biological indicator subjected to the same sterilization process.

The methods described herein can be performed by determining dipicolinic acid release continuously, periodically, or at selected time points during a run of a sterilization process. It is known that release of dipicolinic acid from spores continues during the period during which the spores are being inactivated by the sterilization process, and therefore likely continues for at least a short period thereafter. For this reason, an increase in the release of dipicolinic acid between a first measurement and a subsequent measurement is a conservative indication that the spore inactivation is continuing and that viable spores remain in the biological indicator. Thus, in an alternative method of assessing the effectiveness of a sterilization treatment, dipicolinic acid released from spores of a biological indicator is assessed over a period of time, and the effectiveness of sterilization can be defined as a sufficient sterilization treatment such that the rate of change of the release of dipicolinic acid over time decreases to a selected value, or that the release of dipicolinic acid substantially or completely stops.

The invention also relates to kits that are useful in the methods described. The kit comprises at least a biological indicator described herein (i.e., one comprising spores which contain DPA and, optionally, a lanthanide salt). The kit can also comprise either a control sample (which may be a positive or a negative control) and/or a written or graphical material.

The control sample comprises an amount of DPA that is correlated with the amount of DPA in the spores of the biological indicator. The amount of DPA in the control sample can, for example, be equal to (or a known multiple or fraction of) the total content of DPA in the spores of the biological indicator. Alternatively, the amount of DPA in the control sample can be equal to (or a known multiple or fraction of) the amount of DPA released from the spores of the biological indicator when a certain degree of loss of viability has occurred. Thus, the absolute amount of DPA released from the spores of the biological indicator need not be determined. Instead, the amount of DPA released from the spores of the biological indicator can be compared with the amount of DPA in the control sample in order to provide a qualitative (i.e., relative) assessment of the relative DPA release or the relative viability loss. The form of DPA in the control sample can be varied, provided that the concentration of DPA can be consistently determined correctly. The control sample can, for example, comprise DPA in spores, DPA in water or a buffer solution, or DPA in an aliquot of spores that have been treated in a way that has inactivated a selected percentage (e.g., substantially 100%) of the spores.

When the control sample comprises inactivated spores, it is preferred that the spores were inactivated using the same sterilization method to be assessed using the biological indicator. Also, when the control sample comprises spores, it is preferred that the spores be derived from the same organism, and more preferably from the same batch of spores, as the spores of the biological indicator.

The written or graphical material describes the relationship between release of DPA from spores of the biological indicator and loss of viability of a microorganism subjected to the same sterilization treatment as the spores (i.e., loss of viability of the spores of the biological indicator or loss of viability of one or more other microorganisms). These written or graphical materials are preferably prepared based on assays performed using the same batch of spores as the spores of the biological indicator. The format of the written or graphical material may be variable, and may be communicated by any media, including paper or electronic media. It may be included as a published document, in an electromagnetic form (in the form of a recorded audio or video production, a computer file, or electromagnetic impulses in an electrical device such as a computer or integrated circuit), or in any other tangible medium of expression. A kit may contain written or graphical material, in electronic form or electromagnetic form that provides a positive or/a negative control, such that one practicing the invention can compare the positive and/or negative control with the quantity of DPA released from the spores of the biological indicator, in order to assess the effectiveness of a sterilization process.

The kit can also comprise an analyzer for assessing DPA released from the biological indicator. The appropriate analyzer will depend on the assay format to be used, and the analyzer for substantially any DPA assay can be included in the kit. For example, when DPA is to be assessed by DUVS, the analyzer should be a spectrophotometer capable of performing scans of absorbance values over a variety of wavelengths (i.e., a "scanning" spectrophotometer). The biological indicator and the control sample can each be adapted to fit the analyzer (e.g., each can be contained in a disposable, optically clear cuvette for DUVS analysis). Optically-clear cuvettes can include plastic, glass, quartz cuvettes, vials and glass slides.

In one embodiment, the kit comprises a biological indicator, a control sample, and an analyzer for comparing the amount of DPA released from spores of the biological indicator with the amount of DPA in the control sample. The amount of DPA in the control sample is correlated with the amount of DPA released from the spores of the biological indicator upon achieving a desired decrease in spore viability. When the amount of DPA released from the spores of the biological indicator surpasses the amount of DPA in the control sample (or a multiple or fraction of that amount), the analyzer can produce a visual, audible, or electronic signal to indicate that this has occurred. If the signal is an electronic signal, for example, it can trigger the end of the sterilization process. Similarly, an audible or visual signal can indicate to an operator that the desired degree of sterility has been achieved and that the sterilization process may be halted.

The invention is now described with reference to the following non-limiting examples. These examples are provided for the purpose of illustration only and the invention is not limited to these examples, but rather encompass all variations which are evident as a result of the teaching provided herein.

EXAMPLE 1

Duplicates of three (3) biological indicators (BIs) of the invention were designated "C", "A2", and "A15." Each was a 20 milliliter borosilicate glass scintillation vial containing $10^6$ air-dried spores of *Bacillus subtilus*. The vials were subjected to a moist heat sterilization process by autoclave (15 p.s.i.g. steam, 121° C.), as follows:

| Biological Indicator (BI) | Duration of Sterilization Process |
|---|---|
| C | 0 minutes |
| A2 | 2 minutes |
| A15 | 15 minutes |
| A30 | 30 minutes |

The release of DPA of the spores of each BI was determined as follows. The vials were removed from the autoclave, allowed to cool to approximately room temperature, and 10 milliliters of deionized, distilled water was added to each vial. The vials were vortexed and subsequently sonicated for one minute to suspend the spore debris and to dissolve any released DPA.

The absorbance of each suspension was then assessed using standard quartz cuvettes, by scanning photospectrometry, performed at wavelengths including about 200–400 nanometers using a Hewlett Packard 8453 UV-VIS transmission spectrophotometer, model USP-2000, available from Hewlett Packard, Palo Alto, Calif., U.S.A.

Figure 2:
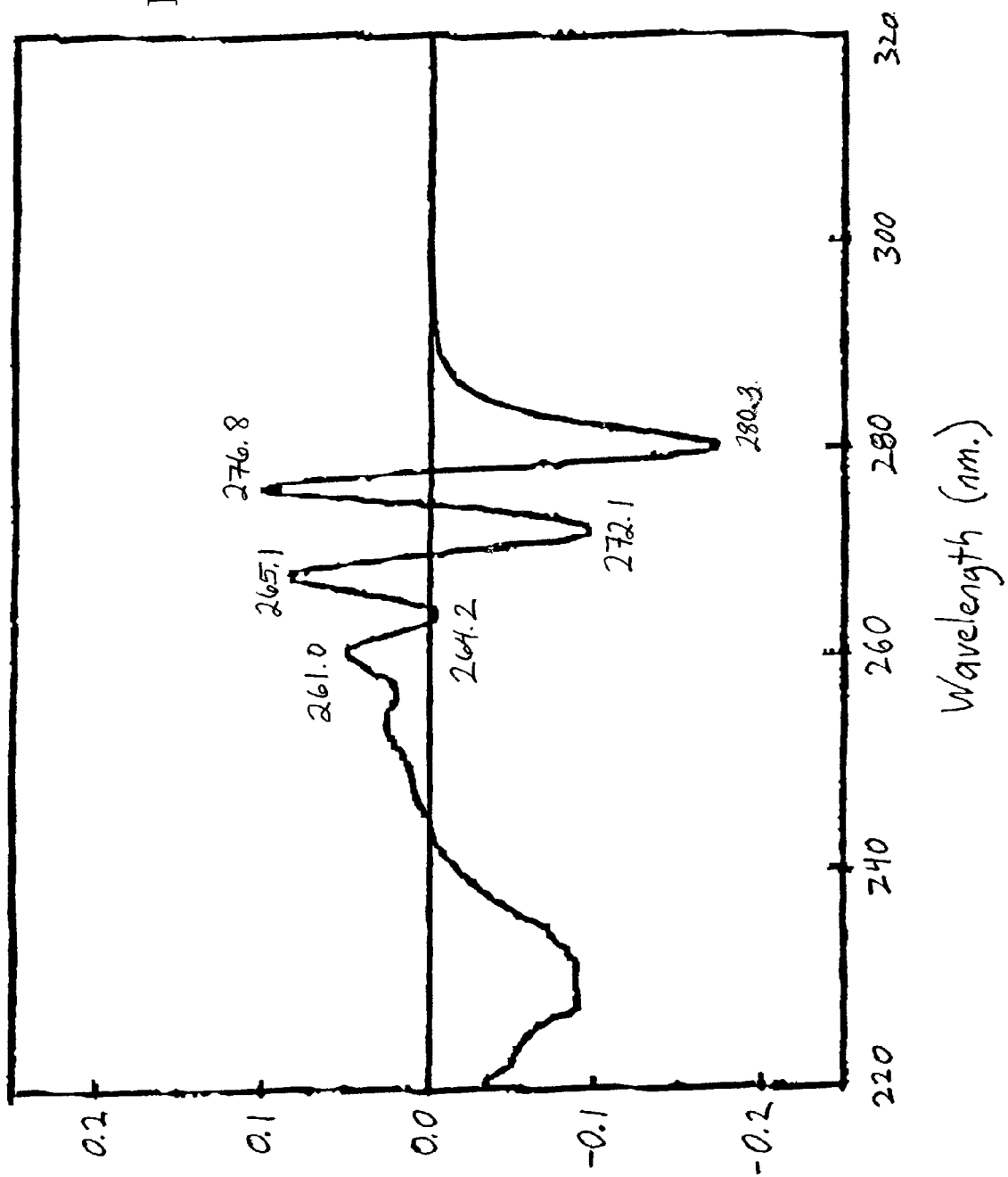
FIG. 2 is a derivative spectrum (d{absorbance}/d{wavelength}; $dA/d\lambda$) of a 0.15 millimolar solution of calcium dipicolinate. Derivative maxima and minima occur at 261.0, 265.1, and 276.8 nanometers and at 264.2, 272.1, and 280.3, respectively, as described in Warth (1983, Anal. Biochem. 130:502–505).
Figure 3:
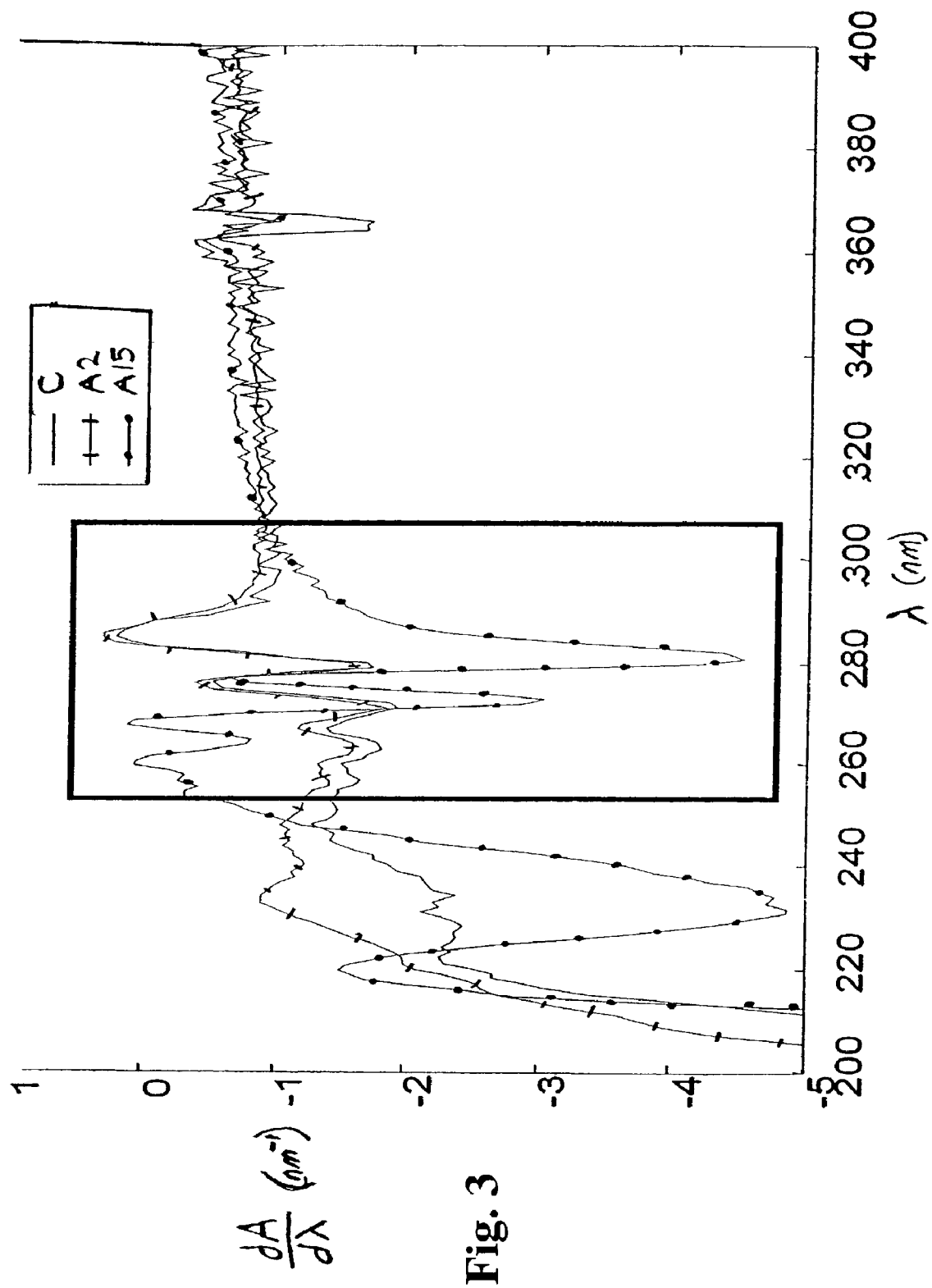
FIG. 3 is a derivative spectrum ($dA/d\lambda$,) of three spore preparations stored in liquid scintillation vials. Suspension C was not autoclaved. Suspension A2 was autoclaved for 2 minutes. Suspension A15 was autoclaved for 15 minutes.
Figure 4:
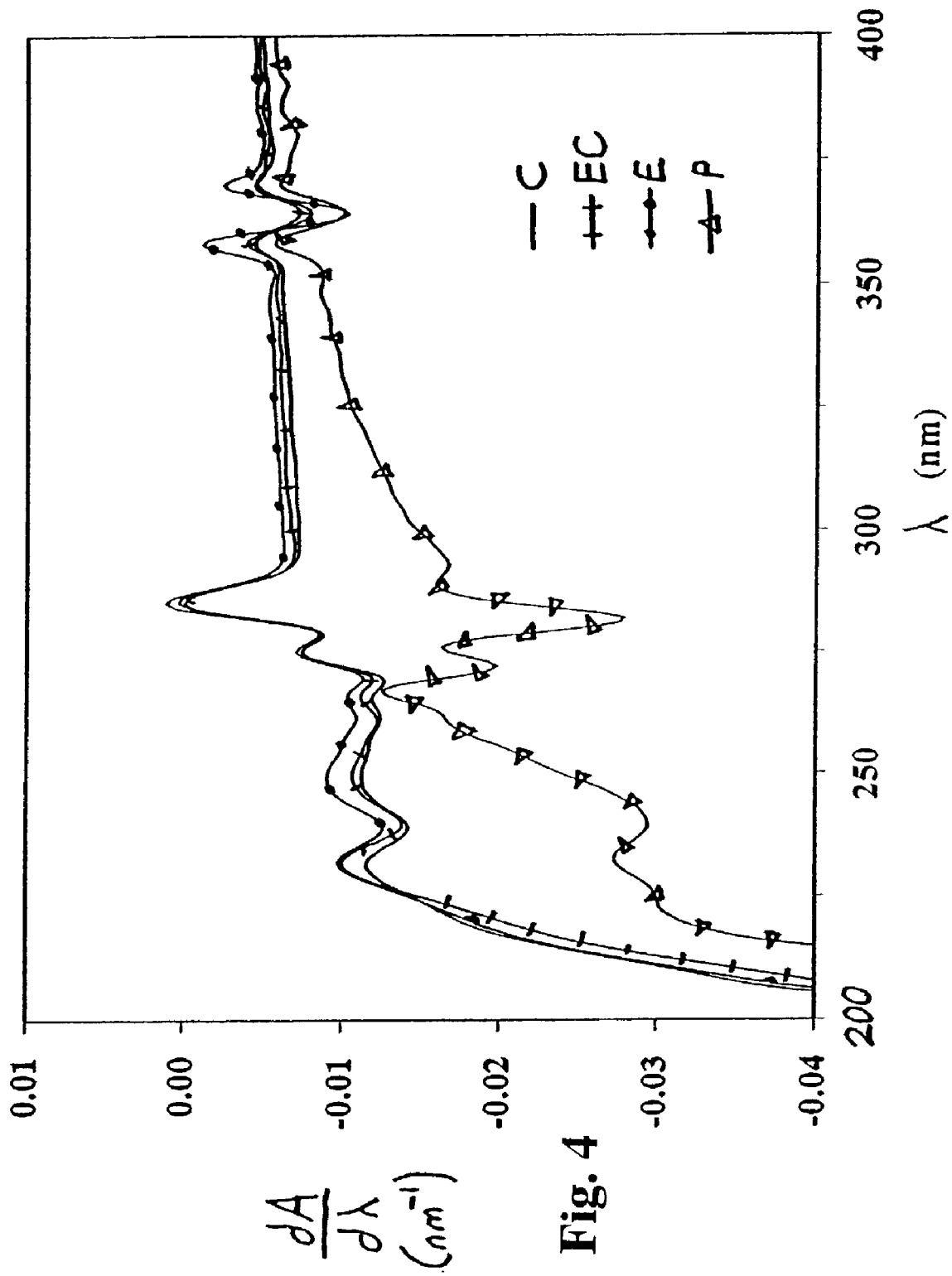
FIG. 4 is a derivative spectrum ($dA/d\lambda$) of six spore preparations that were stored in liquid scintillation vials. Suspension C was not subjected to any sterilization treatment. Suspension EC was subjected to a mixture of ethylene oxide and chlorofluorohydrocarbon gas (CFH). Suspension E was subjected to ethylene oxide alone. Suspension P was subjected to hydrogen peroxide plasma.

The absorbance data was subjected to first derivative analysis (with respect to wavelength) and can be seen in FIG. 3. A comparison of FIG. 2 (a first derivative spectrum (d{absorbance}d{wavelength}; $dA/d\lambda$,) of a 0.15 millimolar solution of calcium dipicolinate) and FIG. 3 indicates that the derivative spectra of the spore suspensions obtained from the autoclaved BIs (A2 and A15) exhibit spectral changes that are characteristic of DPA, correlating with parallel viability data (shown below) which demonstrated that spores of A2 and, particularly A15, were rendered non-viable. Wavelengths at which the change in derivative spectra bear a close correlation to degree of spore inactivation include about 220, 235, 260, 268, and 280 nanometers. The wavelength at 276 nanometers also shows this correlation.

Standard spore viability assays were performed on each of the spore populations of the BIs, post-sterilization process, and resulted in the following viability data:

| Biological Indicator (BI) | % Viability of Spores |
|---|---|
| C | ~100% |
| A2 | ~15% |
| A15 | ~0% |

Thus, a greater than six log kill was achieved in the sterilization process in which the biological indicator A15 was included.

EXAMPLE 2

Four biological indicators (BIs) of the invention, designated "C", "EC", "E", and "P" were subjected to the following sterilization process:

(i) BI "C" was not subjected to any sterilization process;

(ii) BI "EC" was treated by applying a mixture of ethylene oxide (90%) and CFH (10%) for 130 minutes in a model 2047 90/10 OXYFUME® sterilizer (Vacudyne, Inc., Chicago Heights, Ill., U.S.A.);

(iii) BI "E" was treated by application of pure ethylene oxide for sixty-two minutes in a model 300 3M® sterilizer (3M, St. Paul, Minn., U.S.A.); and (iv) BI "P" was treated by application of hydrogen peroxide plasma (45–59.5% $H_2O_2$, balance water vapor (STERRAD®) for about thirteen minutes.

Figure 5:
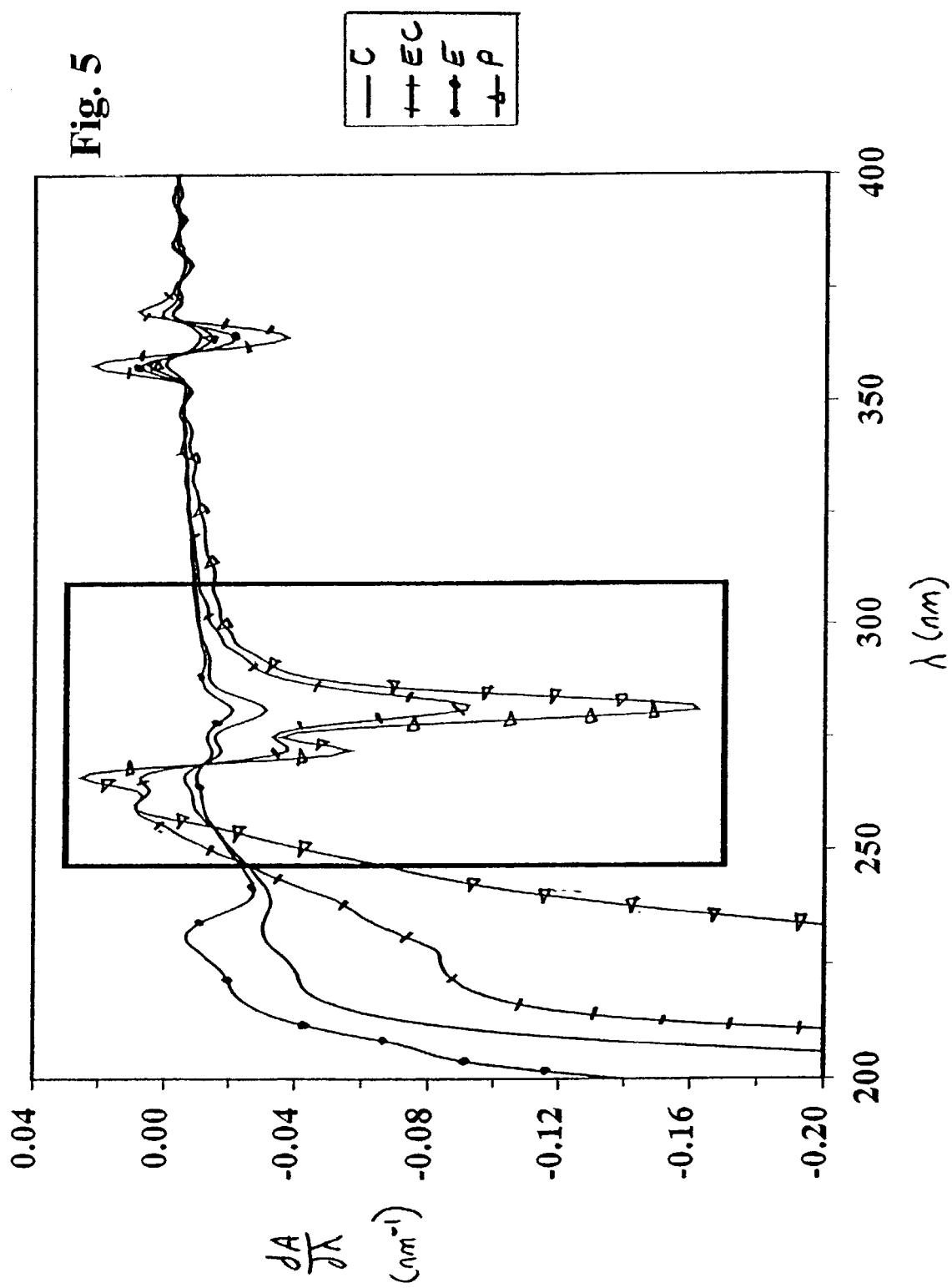
FIG. 5 is a derivative spectrum ($dA/d\lambda$,) of four spore suspensions which were adsorbed onto nylon or cellulose acetate filters. Suspension C was not subjected to any sterilization treatment. Suspension EC was subjected to a mixture of ethylene oxide and CFH. Suspension E was subjected to ethylene oxide alone. Suspension P was subjected to hydrogen peroxide plasma.

A first derivative spectrum obtained by DUVS analysis is shown in FIG. 5.

Each BI was a glass vial containing $10^8$ spores of *B. subtilis*. Viability assessments done by standard procedures (plate counts) showed that for each BI, the survival of the spores was about $0.3 \times 10^7$ (about a 6.67 log kill).

EXAMPLE 3

Four BIs were prepared by adsorbing about 108 spores onto one surface of NALGENE® model 195–2520 syringe filter membranes (25 millimeters in diameter; pore size 0.2 micrometer; nylon membrane), or NALGENE® model 190-2520 syringe filter membranes (25 millimeters in diameter; pore size 0.2 micrometer; cellulose acetate membrane, air dried under sterile conditions for 24 hours). Membranes sold under the trademark NALGENE are available from Nalge Nunc, Intl., Rochester, N.Y., U.S.A.

Each of the BIs, designated "C", "EC", "E" or "P" was subjected to a different sterilization treatment:

(i) BI "C" was not subjected to any treatment, (ii) BI "EC" was treated by application of a mixture of 90% ethylene oxide and 10% CFH for a period of 130 minutes, (iii) BI "E" was treated by application of pure ethylene oxide for a period of 62 minutes, and (iv) BI "P" was treated by application of hydrogen peroxide plasma (STERRAD®) for an exposure period of 13 minutes and 10 seconds (with an entire cycle of 70 minutes).

Figure 6:
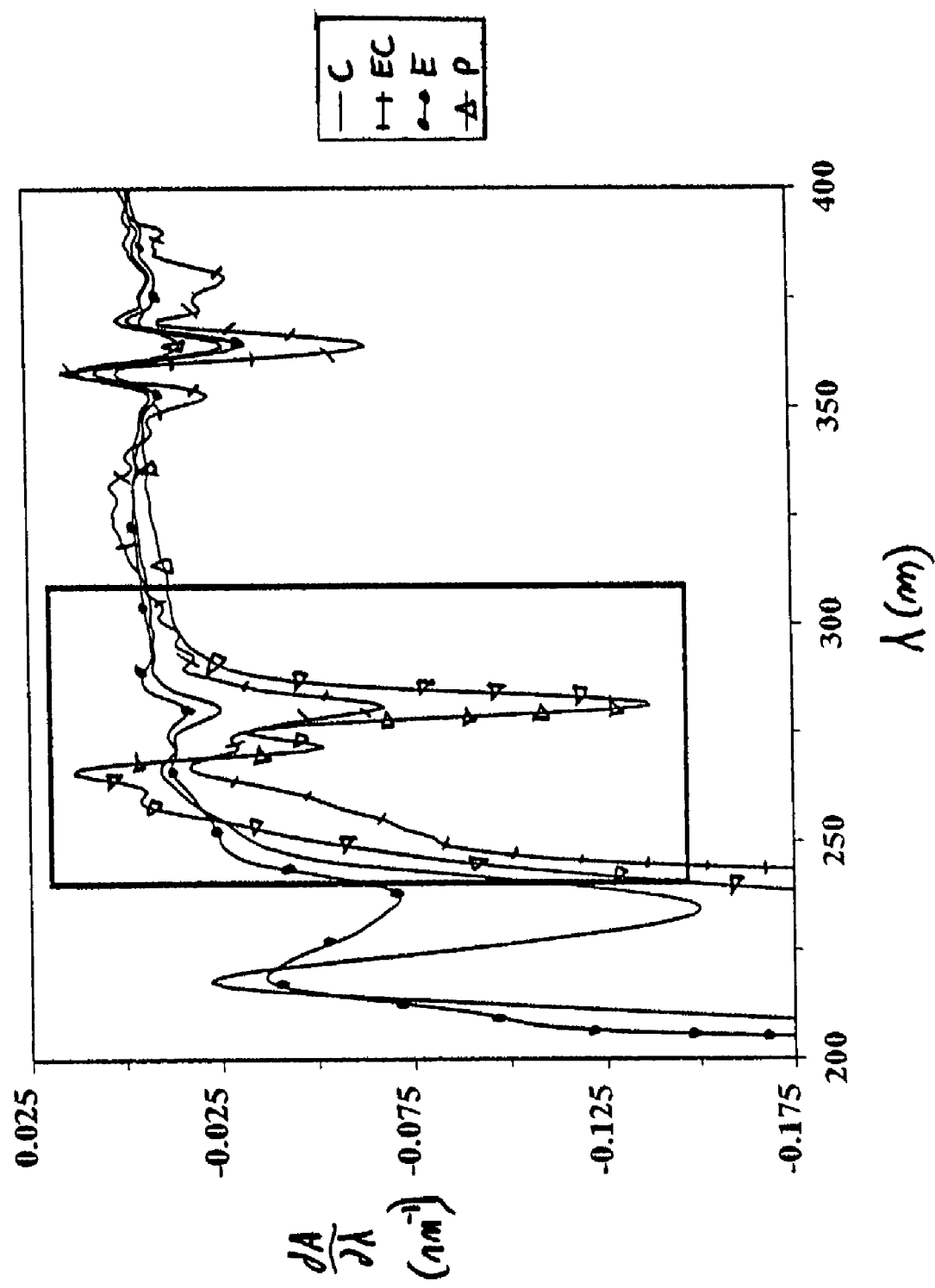
FIG. 6 is a derivative spectrum ($dA/d\lambda$) of four spore suspensions which were subjected to different sterilization processes: untreated, 100% EtO, 90% EtO/10% CFH, and hydrogen oxide plasma.

A first derivative absorbance curve obtained by DUVs analysis of spores from each of the BIs was obtained upon completion of the selected sterilization process, and is shown in FIG. 6. In these samples, survival of spores was approximately the same for the various treatment methods, and fractional survival of spores was equal to about $0.33 \times 10^{-7}$ (i.e., about 1 of the original $10^8$ spores), showed survival on each of three viability plates at a 10 plating dilution.

EXAMPLE 4

BIs were prepared by adsorbing about $10^8$ *B. subtilis* spores onto one surface of DURAPORE® PVDF membranes (Millipore Corporation, Bedford, Mass., U.S.A; 25 millimeter diameter, pore size 0.1 micrometer, contained in the MILLEX®-VV Sterilizing Filter unit), air-dried under sterile conditions for 24 hours, and individually subjected to one of four treatments. The biological indicator designated "C was not subjected to any sterilization process. The remaining were treated as follows:

(i) BI "EC" was treated by application of a mixture of 90% ethylene oxide and 10% CFH for a period of 95 minutes, (ii) BI "E" was treated by application of pure ethylene oxide for a period of 62 minutes, and (iii) BI "P" was treated by application of hydrogen peroxide plasma (STERRAD®) for a period of 13 minutes and 10 seconds. In these samples, survival of spores was approximately the same for the various treatment methods, and fractional survival of spores was equal to about $0.33 \times 10^7$. A first derivative spectrum of each of the spore suspensions obtained by DUVS is shown in FIG. 6.

EXAMPLE 5

Five BIs (20 ml glass vials, each containing about $10^7$ air-dried spores obtained from *Bacillus subtilis* and a terbium salt) were each subjected to an autoclave sterilization process for different durations of time, 0 minutes, four minutes, eight minutes and sixteen minutes.

Figure 7:
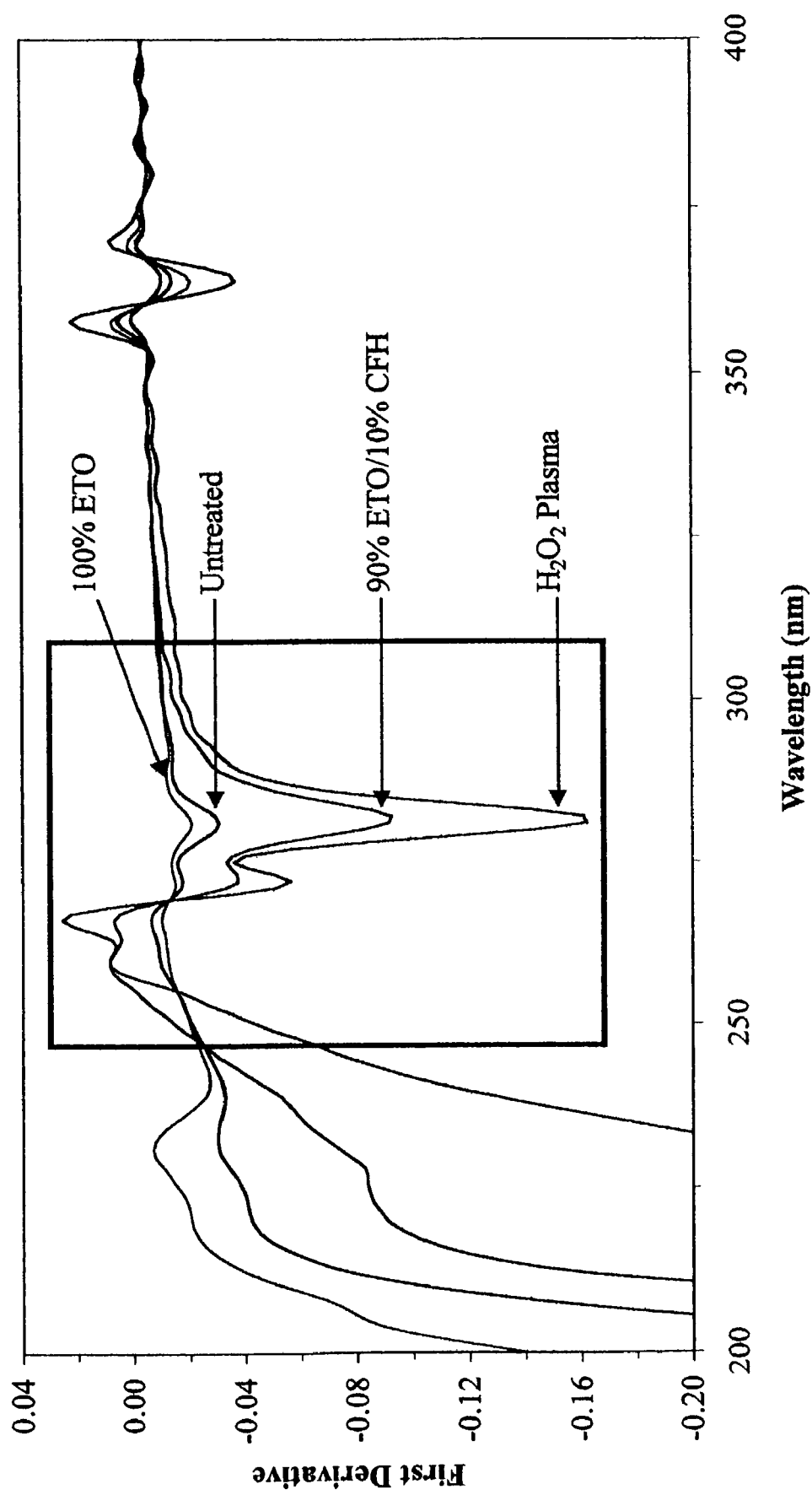
FIG. 7 is a derivative spectrum ($dA/d\lambda$) of four spore suspensions which were adsorbed onto PVDF filters. Suspension C was not subjected to any sterilization treatment. Suspension EC was subjected to a mixture of ethylene oxide and CFH (90%/10%). Suspension E was subjected to ethylene oxide alone. Suspension P was subjected to hydrogen peroxide plasma.

FIG. 7 illustrates the kinetics of DPA release from the spores of each of the autoclaved BIs. As can be seen, autoclaving for approximately fifteen minutes resulted in a 6-log kill.

Figure 8:
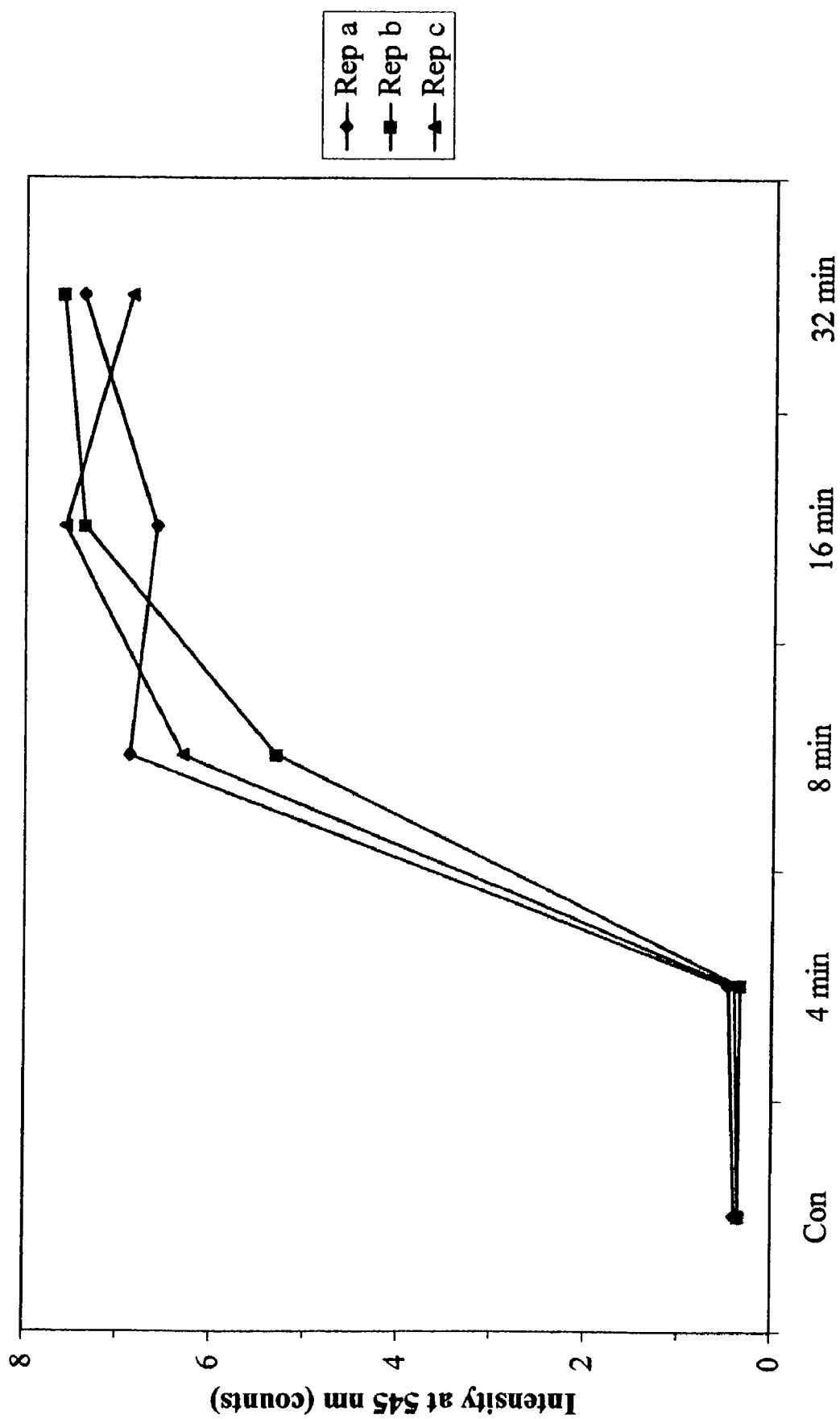
FIG. 8 shows intensity of free dipicolinic acid released from an autoclaved spore suspension taken at four time intervals throughout the autoclaving process at 545 nanometers, in the presence of ionized terbium.
Figure 9:
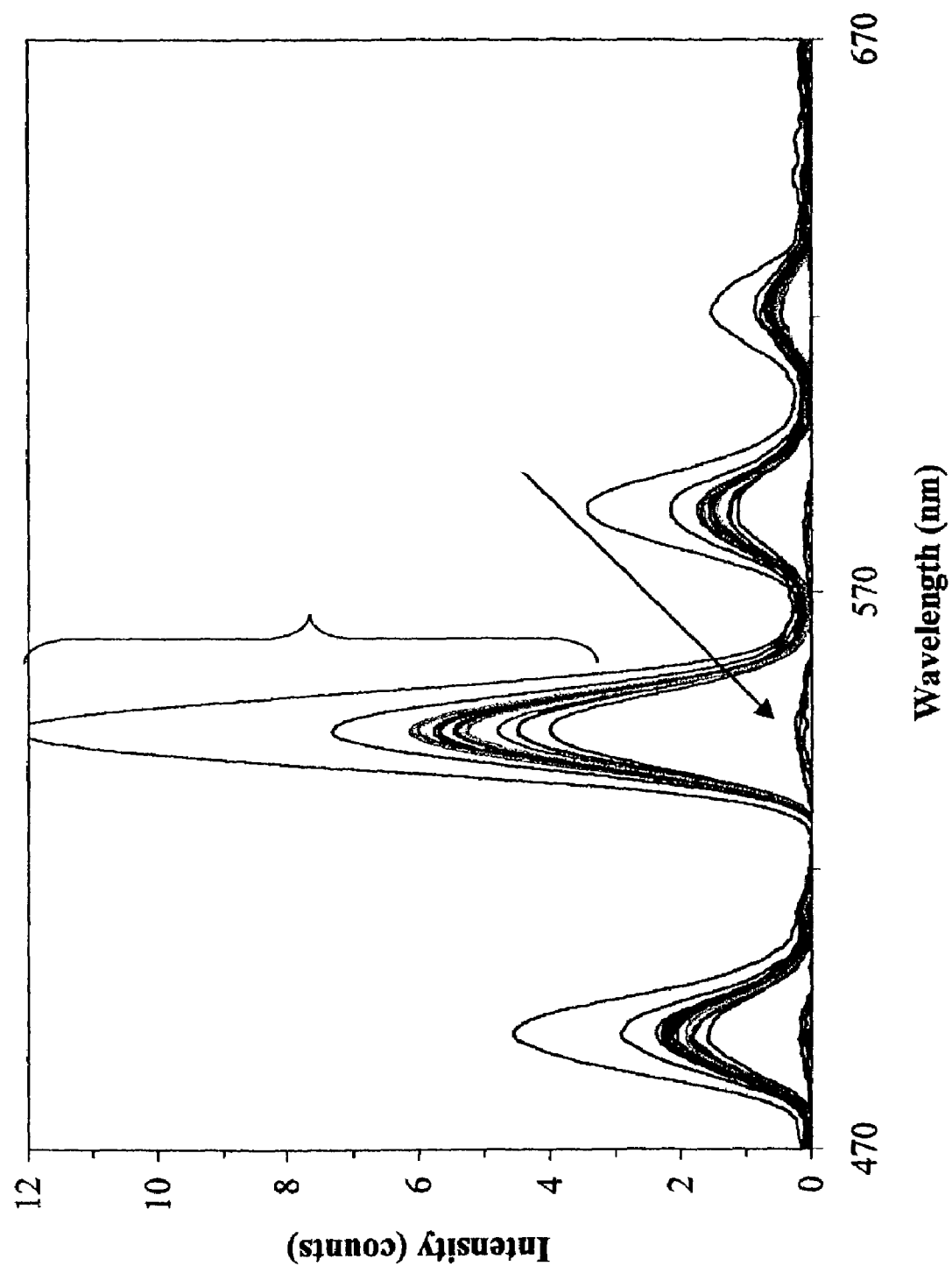
FIG. 9 is a plot showing intensity versus wavelength (nm) of spore suspensions (B. subtilis) treated with a hydrogen peroxide gas plasma sterilization process (STERRAD®) and assayed in the presence of ionized terbium.

In FIG. 8 the emission data obtained from the spores of each of the above-treated BIs is shown, assayed in the presence of ionized terbium. The peak emission intensity occurs at about 545 nanometers, with minor peaks at about 480, 580, and 600 nanometers.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for assessing the effectiveness of a sterilization process, the method comprising:
   a) providing a biological indicator comprising a quantity of spores that comprise dipicolinic acid, wherein the biological indicator has a threshold amount of dipicolinic acid or a threshold rate of release of dipicolinic acid from the spores that has been predetermined to correlate to death of the quantity of spores;
   b) subjecting the biological indicator to a sterilization process
   c) determining an amount of the dipicolinic acid or a rate of a release of the dipicolinic acid from the spores after the sterilization process; and
   d) comparing at least one of
      (i) the amount of the dipicolinic acid after the spores have been subjected to the sterilization process with the threshold amount of dipicolinic acid to determine whether the amount of the dipicolinic acid after the spores have been subjected to the sterilization process is at least or greater than the threshold amount of dipicolinic acid; and
      (ii) the rate of the release of the dipicolinic acid from the spores after the spores have been subjected to the sterilization process with the threshold rate of release of dipicolinic acid to determine whether the rate of release of the dipicolinic acid after the spores have been subjected to the sterilization process is at least or less than the threshold rate of release of dipicolinic acid from the spores;
   whereby if the amount of the dipicolinic acid after the spores have been subjected to the sterilization process is at least or greater than the threshold amount of dipicolinic acid or the rate of the release of the dipicolinic acid from the spores after the spores have been subjected to the sterilization process is at least or less than the threshold rate of release of dipicolinic acid from the spores, death of the quantity of spores in the biological indicator is confirmed and the sterilization process is effective.

2. The method of claim 1, further comprising:
   (e) assessing viability of the spores.

3. The method of claim 2, wherein the viability of the spores is assessed by analyzing visible light scattering of a suspension of the spores.

4. The method of claim 2, wherein the viability is assessed by multi-angle light scattering analysis of a suspension of the spores.

5. The method of claim 2, wherein the viability is assessed by culturing the spores under conditions conducive to the germination and subsequent vegetative proliferation of the organism from which the spores were obtained.

6. The method of claim 2, wherein the biological indictor further comprises a growth medium.

7. The method of claim 1, wherein the sterilization process of step (b) is a low temperature sterilization process.

8. The method of claim 1, wherein the sterilization process of step (b) is selected from the group consisting of a heat sterilization process, a moist heat sterilization process, and a gas plasma sterilization process.

9. The method of claim 1, wherein the sterilization process of step (b) is selected from a peracetic acid sterilization process, a formaldehyde sterilization process, an iodine sterilization process, a glutaraldehyde sterilization process, a nitrous acid sterilization process, an ethylene oxide sterilization process, and a hypochlorous acid sterilization process.

10. The method of claim 1, wherein the spores are selected from spores of a bacterium of the genus *Bacillus* and spores of a bacterium of the genus *Clostridium*.

11. The method of claim 1, wherein the spores are selected from spores of *Bacillus subtilis*, spores of *Clostridium sporogenes*, and spores of *Bacillus stearothermophilus*.

12. The method of claim 1, wherein the spores are selected from spores of *Bacillus anthracis* and spores of a bacterium of the genus *Sporosarcine*.

13. The method of claim 1, wherein the biological indicator is a container having the spores contained therein.

14. The method of claim 13, wherein the container is selected from a vial, a capsule, a dish, an ampoule, a sponge, a box, an envelope, a manually-openable packet, and a manually tearable packet.

15. The method of claim 1, wherein the biological indicator is a member to which the spores are adsorbed, and the member is selected from the group consisting of a film, a sheet, a membrane, a vial, fibers, textiles and a stick.

16. The method of claim 1, wherein the biological indicator further comprises a lanthanide salt.

17. The method of claim 16, wherein the lanthanide salt is a terbium salt.

18. The method of claim 1, wherein the rate of release of the dipicolinic acid from the spores is determined by chromatographic analysis.

19. The method of claim 18, wherein the chromatographic analysis is selected from the group consisting of gas chromatographic analysis, thin layer chromatographic analysis, and high pressure chromatographic analysis.

20. The method of claim 1, wherein the rate of release of the dipicolinic acid from the spores is determined by derivative spectroscopic analysis.

21. The method of claim 20, wherein the spectroscopic analysis is accomplished by assessing an absorbance at approximately 545 nanometers.

22. The method of claim 1, wherein the rate of release of the dipicolinic acid from the spores is determined by derivative ultraviolet spectroscopic analysis.

23. The method of claim 22, wherein the derivative ultraviolet spectroscopic analysis is accomplished by assessing a derivative absorbance at an approximate wavelength selected from the group consisting of 220 nanometers, 235 nanometers, 260 nanometers, 268 nanometers, 276 nanometers, and 280 nanometers.

24. The method of claim 1 wherein step (c) further comprises:
   (i) contacting the spores with a fluid, and
   (ii) assessing the presence or absence of dipicolinic acid in the fluid.

25. The method of claim 24, wherein the fluid of step (c) (ii) comprises a lanthanide ion.

26. The method of claim 25, wherein the lanthanide ion is a terbium ion.

27. The method of claim 1, wherein step (b), step (c) and step (d) are carried out substantially simultaneously.

28. The method of claim 27, wherein the sterilization process of step (b) is halted when the amount of the dipicolinic acid from the spores reaches the threshold amount.

29. The method of claim 27, wherein the sterilization process of step (b) is halted when the rate of release of the dipicolinic acid declines to the threshold rate of release.

30. The method of claim 1, wherein the determination of the amount of the dipicolinic acid or the rate of the release of the dipicolinic acid is carried out at multiple time points during step (c).

31. A method for assessing the effectiveness of a disinfection process, the method comprising:
   a) providing a biological indicator comprising a quantity of spores that comprise dipicolinic acid, wherein the biological indicator has a threshold amount of dipicolinic acid or a threshold rate of release of dipicolinic acid from the spores that has been predetermined to correlate to death of the quantity of spores;
   b) subjecting the biological indicator to a disinfection process
   c) determining an amount of the dipicolinic acid or a rate of a release of the dipicolinic acid from the spores after the disinfection process; and
   d) comparing at least one of
      (i) the amount of the dipicolinic acid after the spores have been subjected to the disinfection process with the threshold amount of dipicolinic acid to determine whether the amount of the dipicolinic acid after the spores have been subjected to the sterilization process is at least or greater than the threshold amount of dipicolinic acid; and
      (ii) the rate of the release of the dipicolinic acid from the spores after the spores have been subjected to the disinfection process with the threshold rate of release of dipicolinic acid to determine whether the rate of release of the dipicolinic acid after disinfection is at least or less than the threshold rate of release of dipicolinic acid from the spores;
   whereby if the amount of the dipicolinic acid after the spores have been subjected to the disinfection process is at least or greater than the threshold amount of dipicolinic acid or the rate of the release of the dipicolinic acid from the spores after the spores have been subjected to the disinfection process is at least or less than the threshold rate of release of dipicolinic acid from the spores, death of the quantity of spores in the biological indicator is confirmed and the disinfection process is effective.

32. A method for assessing the effectiveness of a sterilization process, the method comprising:
   a) providing a biological indicator comprising a quantity of spores that comprise dipicolinic acid, wherein the biological indicator has a threshold amount of dipicolinic acid from the spores that has been predetermined to correlate to death of the quantity of spores;
   b) subjecting the biological indicator to a sterilization process,
   c) determining an amount of the dipicolinic acid from the spores after the sterilization process; and
   d) comparing the amount of the dipicolinic acid from the spores after the spores have been subjected to the sterilization process with the threshold amount of dipicolinic acid to determine whether the amount of dipicolinic acid after sterilization is at least or greater than the threshold amount of dipicolinic acid, whereby if the amount of the dipicolinic acid after the spores have been subjected to the sterilization process is at least or greater than the threshold amount of dipicolinic acid, death of the quantity of spores in the biological indicator is confirmed and the sterilization process is effective.

33. A method for assessing the effectiveness of a disinfection process, the method comprising:
   a) providing a biological indicator comprising a quantity of spores that comprise dipicolinic acid, wherein the biological indicator has a threshold amount of dipicolinic acid from the spores that has been predetermined to correlate to death of the quantity of spores;
   b) subjecting the biological indicator to a disinfection process
   c) determining an amount of the dipicolinic acid from the spores after the disinfection process; and
   d) comparing the amount of the dipicolinic acid from the spores after the spores have been subjected to the disinfection process with the threshold amount of dipicolinic acid to determine whether the amount of dipicolinic acid after disinfection is at least or greater than the threshold amount of dipicolinic acid, whereby if the amount of the dipicolinic acid after the spores have been subjected to the disinfection process is at least or greater than the threshold amount of dipicolinic acid, death of the quantity of spores in the biological indicator has occurred and the disinfection process is effective.

* * * * *